United States Patent [19]

Arcamone et al.

[11] 4,112,076

[45] Sep. 5, 1978

[54] EPI-DAUNOMYCIN AND EPI-ADRIAMYCIN COMPOUNDS AND METHOD OF USE

[75] Inventors: Federico Arcamone, Nerviano, Milan; Alberto Bargiotti, Milan; Aurelio di Marco, Milan; Sergio Penco, Milan, all of Italy

[73] Assignee: Societa' Farmaceutici Italia S.p.A., Milan, Italy

[21] Appl. No.: 675,696

[22] Filed: Apr. 9, 1976

[30] Foreign Application Priority Data

Apr. 30, 1975 [GB] United Kingdom ............... 18098/75

[51] Int. Cl.$^2$ ....................... A61K 31/70; C07H 15/24
[52] U.S. Cl. ........................................ 424/180; 536/4; 536/17; 536/18; 536/122
[58] Field of Search ....................... 536/17, 4; 424/180

[56] References Cited

U.S. PATENT DOCUMENTS

| | | | |
|---|---|---|---|
| 3,803,124 | 4/1974 | Arcamone et al. | 536/17 |
| 4,025,623 | 5/1977 | Arcamone et al. | 536/17 |
| 4,046,878 | 9/1977 | Patelli et al. | 536/17 |

*Primary Examiner*—Johnnie R. Brown
*Attorney, Agent, or Firm*—Hubbell, Cohen, Stiefel & Gross

[57] ABSTRACT

Disclosed is a process for preparing glycoside antitumor antibiotics, including the known compounds daunomycin, adriamycin, 4'-epi-daunomycin and 4'-epi-adriamycin and the novel antibiotics, 3',4'-epi-6'-hydroxydaunomycin, 3',4'-epi-6'-hydroxyadriamycin. 3',4'-epi-daunomycin, 3',4'-epi-adriamycin, 4-demethoxy-4'-epi-daunomycin and 4-demethoxy-4'-epi-adriamycin. Process involves reacting daunomycinone or 4-demethoxy-daunomycinone with a protected 1-halo derivative of 3,4-epi-6-hydroxydaunosamine, 3,4-epi-daunosamine or 4-epi-daunosamine in an inert solvent in the presence of a soluble silver salt catalyst to form a protected derivative of the glycoside antibiotic and removing the protecting groups.

8 Claims, No Drawings

EPI-DAUNOMYCIN AND EPI-ADRIAMYCIN COMPOUNDS AND METHOD OF USE

CROSS-REFERENCE TO RELATED APPLICATIONS

This application is related to and incorporates by reference the contents of co-pending applications, Ser. Nos. 560,104 and 560,105, both filed March 19, 1975, now U.S. Patent Nos. 4,058,519 and 4,039,663; respectively, and Belgian Patent Ser. Nos. 826,848 and 826,978, all of which are owned by the unrecorded assignee hereof.

BACKGROUND OF THE INVENTION

1. Field of the Invention

The present invention relates to glycoside antibiotics of the anthracycline series, processes for their preparation and the use thereof in treating certain tumors in animals.

The Prior Art

British Pat. Nos. 1,003,383 and 1,161,728 which are owned by the unrecorded assignee hereof respectively describe and claim the antibiotics daunomycin and adriamycin.

SUMMARY OF THE INVENTION

This invention relates to glycosides of the anthracycline series. More particularly, the invention provides a new process for the preparation of the well-known antitumor antibiotics daunomycin, adriamycin, 4'-epi-daunomycin and 4'-epi-adriamycin (which are described and claimed respectively in British Patent Specification Nos. 1,003,383 and 1,161,728 and copending U.S. applications, Ser. Nos. 560,105 (filed Mar. 19, 1975), now U.S. Pat. No. 4,039,663 and 560,104 (filed Mar. 19, 1975), now U.S. Pat. No. 4,058,519 all of which are owned by the unrecorded assignee hereof. The invention also relates to the preparation, by said new process of the novel anthracyclinone glycosides: 3',4'-epi-6'-hydroxydaunomycin; 3',4'-epi-6'-hydroxy-adriamycin; 3',4'-epi-daunomycin; 3',4'-epi-adriamycin; 4-demethoxy-4'-epi-daunomycin and 4-demethoxy-4'-epi-adriamycin. These novel anthracyclinone glycosides are also part of the present invention. The novel compounds of the invention are useful in treating certain tumors in animals.

The process of the invention is based on the condensation of a tetracyclic aglycone, having a hydroxy-anthraquinone chromophoric system of the structure (I):

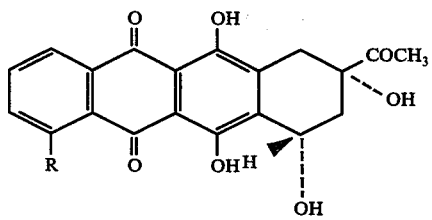

wherein R is methoxy or hydrogen with protected 1-halo derivatives of an amino-deoxy sugar in a suitable organic solvent such as chloroform or methylene chloride in presence of a soluble silver salt catalyst such as silver trifluoro methane sulphonate ($AgSO_3CF_3$) and molecular sieves as dehydrating agents. The solubility of the silver salt in the organic solvents enables the condensation to take place in a homogeneous phase, thereby avoiding the well-known complications of the Köenigs-Knorr reaction in the presence of insoluble silver or mercury compounds. (Gunter Wulff et al, Ang. Chem. Int. Ed. 13, 157 (1974)). The condensation reaction goes to completion in a short time (generally one to eight hours), and the protected glycosides can be obtained in high yield. Moreover, it is very important and quite surprising that the reaction is stereospecific, that is, only the α anomers are formed in the reaction. The reactive protected derivative of the amino-deoxy sugar which is condensed with the aglycone of structure (I) (when R = methoxy) to give the protected glycoside of structure (II):

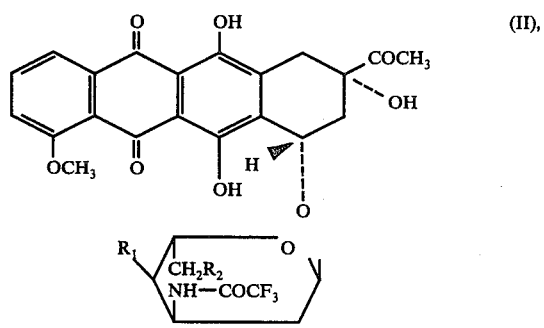

wherein

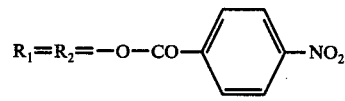

is the novel intermediate: 2,3-dideoxy-4,6-di-O-p-nitro-benzoyl-3-N-trifluoro-acetyl-α-L-ribohexopyranosyl chloride (III), also forming part of the invention:

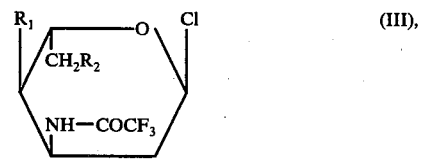

wherein

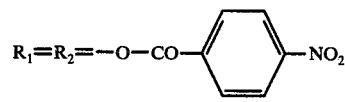

which in turn derives from the 3-amino-2,3-dideoxy-L-ribohexose (3,4-epi-6-hydroxy-daunosamine) (IV):

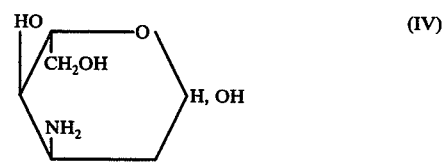

which has previously been unknown in the L-series.

From the protected glycoside (II), after removal of the protecting groups by treatment with a base, the final product (V) is obtained:

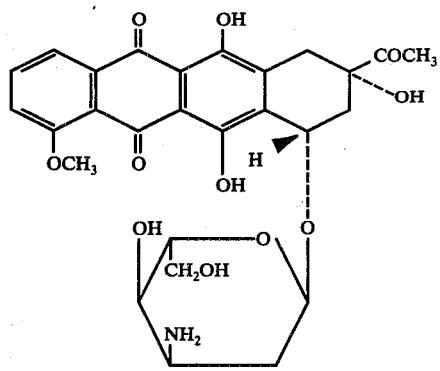
(V)

That is, 3',4'-epi-6'-hydroxy-daunomycin which is isolated as the hydrochloride. Subsequent treatment of compound (V) in accordance with the method described in U.S. Pat. No. 3,803,124 (owned by the unrecorded assignee hereof) affords compounds (VI):

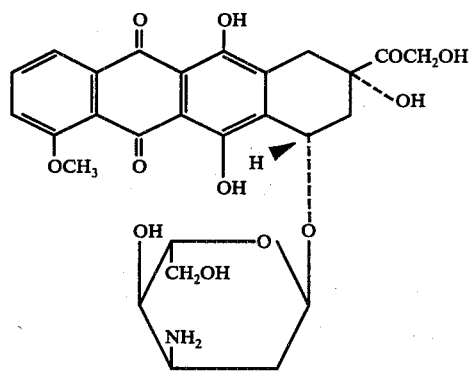
(VI)

that is, 3',4'-epi-6'-hydroxyadriamycin which is also isolated as the hydrochloride. The reactive protected derivative of the amino-deoxy sugar which is condensed with the aglycone of structure (I) (when R = methoxy) to give the protected glycoside of structure (VII):

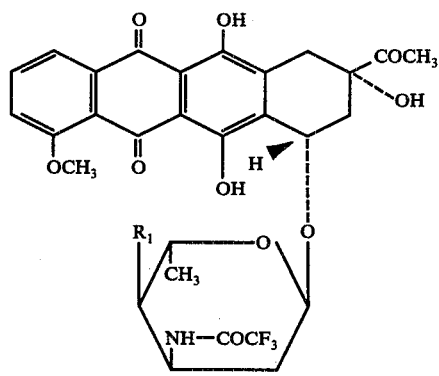
(VII), wherein

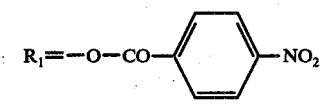

is the new intermediate: 2,3,6-trideoxy-3-N-trifluoroacetyl-4-O-p-nitrobenzoyl-α-L-ribohexo-pyranosyl chloride (VIII):

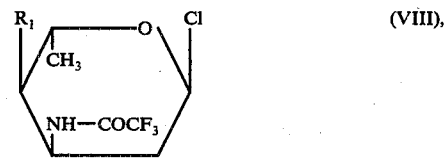
(VIII), wherein

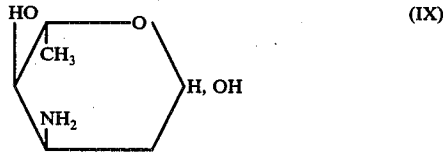

which in turn derives from the 3-amino-2,3,6-trideoxy-L-ribohexose (IX):

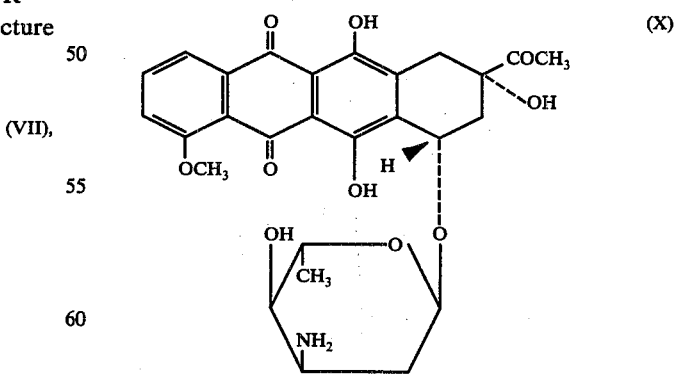
(IX)

which also has been previously unknown in the L-series.

From the protected glycoside (VII), after removal of the protecting groups, the final product (X) is obtained:

(X)

that is, 3',4'-epi-daunomycin which is also isolated as the hydrochloride. The subsequent treatment of compound (X) in accordance with the method described in U.S. Pat. No. 3,803,124 affords the compound (XI):

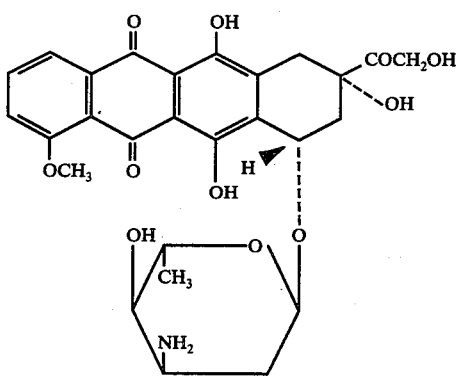

that is, 3',4'-epi-adriamycin which also is isolated as the hydrochloride. When the condensation is carried out by reaction of the aglycone of structure (I) (where R = hydrogen) and a suitable protected derivative of 4-epi-daunosamine, that is, 1-chloro-N,O-di-trifluoroacetyl-4-daunosamine (this intermediate has been described and claimed in copending application Ser. No. 560,105, filed Mar. 19, 1975, now U.S. Pat. No. 4,039,663) the protected glycoside of the structure (XII) is obtained:

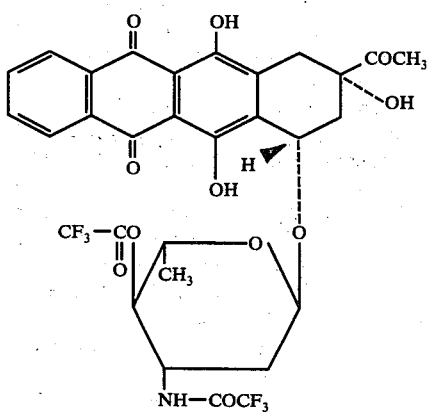

from which, after removal of the protecting groups, first with methanol to obtain the N-trifluoroacetyl derivative and then with dilute NaOH, the final product: 4-demethoxy-4'-epi-daunomycin (XIII) is isolated as the hydrochloride:

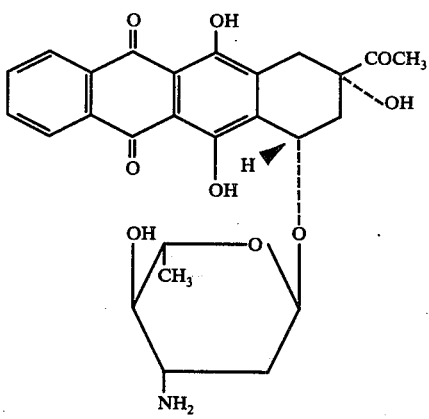

From compound (XIII), following the process described in U.S. Pat. No. 3,803,124, 4-demethoxy-4'-epi-adriamycin (XIV) is obtained as the hydrochloride:

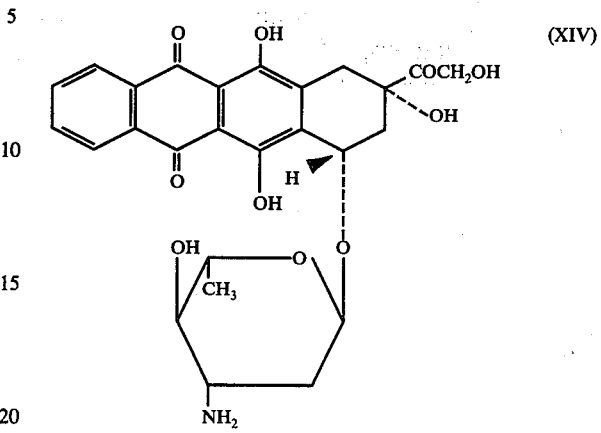

Since the novel condensation process of the invention, which process uses as a catalyst the soluble silver salt $AgSO_3CF_3$ is both a general process and a stereospecific process, it is understood that using the aglycone of formula I (when R = methoxy) the well-known antitumor antibiotics: daunomycin and 4'-epi-daunomycin can be also prepared when the sugar moiety is respectively a suitable protected derivative of daunosamine or 4-epi-daunosamine. The intermediate 2,3-dideoxy-4,6-di-O-p-nitrobenzoyl-3-N-trifluoroacetyl-α-L-ribohexopyranosyl chloride (III) used for the preparation of compound (II) is obtained starting from methyl 4,6-O-benzylidene-2-deoxy-α-L-erythrohexopyranosid-3-ulose (XV) (E.H. Williams et al, Canad. J. Chem. 47, 4467 (1969)).

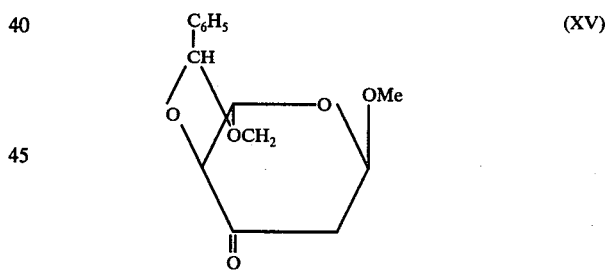

This compound is converted to methyl-2,3-dideoxy-3-N-trifluoroacetyl-α-L-ribohexopyranoside (XVI):

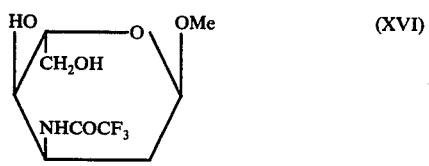

following the procedure described in the literature for the corresponding D isomer (P. J. Beynon et al, J. Chem. Soc. (C), 272 (1969)). Compound (XVI) is subsequently allowed to react with p-nitro-benzoyl chloride in dry pyridine and then with dry hydrogen chloride at 0° C. to obtain 2,3-dideoxy-4,6-di-O-p-nitrobenzoyl-3-N-trifluoroacetyl-α-L-ribohexopyranose (XVII):

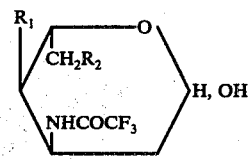

wherein

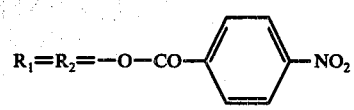

By reacting compound (XVII) again with p-nitrobenzoyl chloride in dry pyridine, its 1,4,6-tri-O-p-nitrobenzoate is isolated from which, after treatment for 1 hour with dry hydrogen chloride at 0° C. in methylene chloride, the desired new compound (III) is finally obtained. The preparation of the other new intermediate 2,3,6-trideoxy-3-N-trifluoroacetyl-4-O-p-nitrobenzoyl-α-L-ribohexo-pyranosyl chloride (VIII) is effected starting from compound (XVI) and following the procedure described by S. Hanessian et al. [Carb. Res. 24, 25 (1972)] for the synthesis of 6-deoxy sugars. By reacting compound (XVI) with N-bromosuccinimide and triphenylphosphine in anhydrous dimethylformamide, its 6-bromo-derivative is obtained, from which by catalytic reduction in the pressure of 20% palladium on charcoal and BaCO$_2$, methyl-2,3,6-trideoxy-3-trifluoroacetamido-α-L-ribohexopyranoside (XVIII) is isolated.

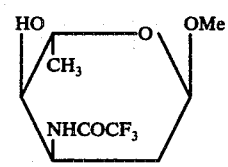

The reaction of compound (XVIII) with p-nitro-benzoyl chloride in dry pyridine affords its 4-O-p-nitrobenzoyl derivative, from which after treatment with dry hydrogen chloride, the 2,3,6-trideoxy-3-N-trifluoroacetyl-4-O-p-nitrobenzoyl-α-L-ribohexopyranose (XIX) is obtained:

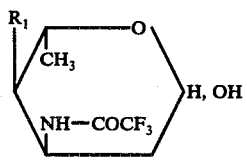

wherein

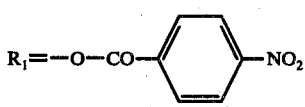

By reacting compound (XIX) again with p-nitro-benzoyl chloride in dry pyridine its 1,4-di-p-nitro-benzoyl derivative is isolated, from which after treatment with dry hydrogen chloride in methylene chloride at 0° C., the desired new compound (VIII) is finally obtained.

DESCRIPTION OF THE PREFERRED EMBODIMENTS

The following examples, in which all parts given are by weight unless otherwise indicated, are given to illustrate the invention, without, however limiting it.

EXAMPLE 1

Preparation of the intermediate: 2,3-dideoxy-4,6-di-O-p-nitrobenzoyl-3-N-trifluoroacetyl-α-L-ribohexopyranosyl chloride III A methanolic solution of hydroxylamine was prepared by treating 8.35 g; 0.12 mol of hydroxylamine hydrochloride with 4.92 g; 0.12 mol of sodium hydroxide in 215 ml of methanol, and filtering off the sodium chloride which formed. To this freshly prepared solution, 5.35 g of 4,6,0-benzylidene-2-deoxy-α-L-erythro-hexo-pyranosid -3-ulose (XV)* were added. After 15 hours at room temperature, the resulting methyl-4,6,0-benzylidene-2-deoxy-α-L-erthro-hexo-pyranosid-3-ulose oxime (5.25 g; 93%) was filtered off, and dried; m.p. 211°-213°; $[\alpha]_D = -201.6°$ ($c = 0.5$ in CHCl$_3$); m/e 247 (M$^+$ −32). The p.r.m. spectrum of this product was consistent with the structure.

*Prepared according to method of E. H. Williams et al, described in Canad. J. Chem. 1969, 47, 4467.

The thusly prepared oxime (5.0 g) in 600 ml of diethyl ether containing an excess of lithium aluminum hydride (2.15 g) was stirred and heated under reflux for 18 hours. Thin layer chromatography (solvent system CHCl$_3$:methanol 6:1 v/v) indicated that the reduction was completed. Addition of ethyl acetate followed by filtration and evaporation afforded the crystalline methyl-3-amino-4,6,0-benzylidene-2,3-dideoxy-α-L-ribohexopyranoside (4.05 g, 85%): m.p. 120°-121° C; $[\alpha]_D = -145°$ ($c = 0.5$ in CHCl$_3$); m/e 265 (M$^+$). This compound (4 g) in 75 ml of 0.5 N methanolic hydrogen chloride was stored at room temperature for one hour. The solution was then adjusted to pH 5.5 with Amberlite ® IR 45 and evaporated to dryness under reduced pressure. The residue was suspended in 70 ml of diethyl ether and treated with 10 ml of trifluoroacetic anhydride at 0° C. overnight. The crude material, obtained by evaporating the suspension to dryness under vacuum until complete removal of the acidity, was treated overnight with methanol at room temperature and gave, after evaporation of the solvent, 3.34 g. (82%) of methyl-2,3-dideoxy-3-N-trifluoroacetyl-α-L-ribo-hexopyranoside (XVI): $[\alpha]_D = -71.35°$ ($c = 0.7$ in CHCl$_3$); m/e 242 (M$^+$ −31). This step follows the procedure of P. J. Beynon et al described in J. Chem. Soc. (C), 1969, 272.

The pyranoside XVI (2.5 g), dissolved in 45 ml of anhydrous pyridine was treated with 4.25 g of p-nitrobenzoyl chloride at 0° C. After two hours the reaction mixture was poured into ice. The precipitate was filtered off and washed with water until neutral. Crystallization from CHCl$_3$-diethyl ether afforded 4.95 g (95%) of the di-p-nitro-benzoate derivative; m.p. 180°-182° C; $[\alpha]_D = -127°$ ($c = 0.48$ in CHCl$_3$). This compound (4 g), dissolved in a mixture of 15 ml of chloroform and 10 ml of acetic acid was saturated with dry hydrogen chloride at 0° C. After 1 hour, the solution was evaporated to dryness under vacuum. In order to completely eliminate the acidity, the residue was dissolved in benzene and evaporated to dryness several times. The purification of the crude product by chromatography on a silica gel column using chloroform as the solvent, afforded 3.15 g (80%) of the pure 2,3-dideoxy-4,6-di-O-p-nitrobenzoyl-3-N-trifluoroacetyl-α-L-ribohexopyranose (XVII); m.p. 114°–116° C; $[\alpha]_D = -124°$ ($c = 0.43$ in $CHCl_3$). The p.m.r. spectrum showed absorption at: 3.83 (d, C-10H), 5.26 (dd, J'4Hz, J" 10.5 Hz, C-4H), and 5.39 δ (s broad, $W_H$ 6Hz, C-1H).

2.5 g of the pyranose (XVII) in 40 ml of anhydrous pyridine were treated with 1.25 g of p-nitrobenzoyl chloride at 0° C.

After 14 hours at room temperature, the reaction mixture was poured into ice. The resulting precipitate, which is the tri-O-p-nitrobenzoyl derivative was filtered off, washed with water to neutrality, and dried under vacuum. The p.m.r. spectrum of the product (2.6 g; 92%), crystallized from $CHCl_3$-diethyl ether; m.p. 168°–170° C, showed inter alia, absorption at 6.72 (s braod, $W_H$ 6Hz C-1H), indicating an axial configuration in the C-1 position of the p-nitrobenzoyl group.

The tri-O-p-nitrobenzoyl derivative (2 g) dissolved in 60 ml of methylene dichloride was saturated with dry hydrogen chloride at 0° C. for one hour. The precipitated p-nitrobenzoic acid was filtered off, and the solution was evaporated to dryness under vacuum until complete removal of the acidity. The resulting crude 2,3-dideoxy-4,6-di-O-p-nitrobenzoyl-3-N-trifluoroacetyl- α-L-ribohexopyranosyl chloride (III) (1.6 g; 95%) was used without further purification. The p.m.r. spectrum of (III) showed, inter alia, absorption of C-1H at 6.45 α (dd, J' 3.5 Hz, J" 1.0 Hz).

EXAMPLE 2

Preparation of the intermediate:
2,3,6-trideoxy-3-N-trifluoroacetyl-4-O-p-nitrobenzoyl- α-L-ribohexopyranosyl chloride (VIII)

A solution of 0.6 g of methyl-2,3-dideoxy-3-N-trifluoroacetyl-α-L-ribopyranoside (XVI) in 14 ml of anhydrous dimethylformamide was mixed with 0.37 g of N-bromo-succinimide and 0.6 g of triphenylphosphine. The reaction mixture was treated for 1 hour at 50° C., and the solution was evaporated under vacuum. The residue was dissolved in 50 ml of chloroform and washed with water to eliminate the succinimide. The crude residue obtained by evaporation of the solvent was purified by chromatography on a column of silicic acid using diethyl ether as the eluting agent.

The thus obtained pure 6-bromo derivative (0.4 g) was dissolved in 40 ml of methanol and reduced in the presence of 0.5 g 20% 20 palladium on charcoal and 2.0 g of barium carbonate at 10 atmospheres to give a quantitative yield of methyl-2,3,6-trideoxy-3-trifluoroacetamido-α-L-ribohexopyranoside (XVIII). Thin layer chromatography of this product on Merck Kieselgel $60F_{254}$ using a $CHCl_3$: methanol solvent system (6:1 v/v) gave an Rf of 0.4. The p.m.r. spectrum was consistent with the structure. This step follows the procedure of S. Hanessian et al, described in Carbohyd. Res. 1972, 24, 45.

A solution of 0.24 g of the pyranoside (XVIII) in 4 ml of anhydrous pyridine was mixed with 0.24 g of p-nitrobenzoyl chloride, the reaction mixture was stirred at 0° C. for 3 hours, and then poured into ice. The thereby formed 4-O-p-nitrobenzoyl derivative was filtered off and washed to neutrality. This compound, after being dried over phosphorous pentoxide for several hours, was dissolved in a mixture of 1 ml of glacial acetic acid and 5 ml of anhydrous methylene dichloride and saturated with dry hydrogen chloride at 0° C. Evaporation of the solvents gave 0.22 g of the 2,3,6-trideoxy-3-N-trifluoroacetyl-4-O-p-nitrobenzoyl-L-ribohexopyranose (XIX). Thin layer chromatography of Merck Kieselgel $60F_{254}$ using a benzene:ethyl acetate solvent system (20:1 v/v) revealed a single spot at Rf 0.18.

A solution of 0.18 g of the pyranose (XIX) in anhydrous pyridine was mixed with 0.13 g of p-nitrobenzoyl chloride, and the mixture was stirred at 0° C. for 3 hours, and then poured into ice. The thus formed di-p-nitrobenzoyl derivative was filtered off and washed to neutrality. This compound was dried, dissolved in 5 ml of dichloromethane and saturated with dry hydrogen chloride at 0° C. Evaporation of the solvent gave a quantitative yield of the desired product: 2,3,6-trideoxy-3-N-trifluoroacetyl-4-O-p-nitrobenzoyl-α-L-ribohexopyranosyl chloride (VIII) which was used without further purification.

EXAMPLE 3

3'-4'-epi-6'-hydroxy-daunomycin (V)

1.1 g of daunomycinone* in 110 ml of anhydrous methylene dichloride were mixed with 0.8 g of 1-chloro-2,3-dideoxy-3-N-trifluoroacetyl-4,6-di-O-p-nitrobenzoyl-α-L-ribohexopyranose (III) in the presence of 12 g of molecular sieve (4 Å Merck) and treated with 0.37 g of $AgSO_3CF_3$ with vigorous stirring overnight at room temperature. The reaction mixture was then neutralized with a saturated aqueous solution of sodium bicarbonate. The organic phase was separated and evaporated under vacuum. The resulting residue was purified by chromatography on a silicic acid column using benzene:ethyl acetate (2:1 v/v) as the eluting system. There were obtain 1.3 g of product (II):m.p. 241°–243°: $[\alpha]_D = +241°$ ($c = 0.07$ in $CHCl_3$).
* Formula I wherein R is methoxy.

The compound (II) (0.7 g), dissolved in 45 ml of acetone was mixed with 50 ml of 0.2 N aqueous sodium hydroxide at 0° C. After 40 minutes, the solution was adjusted to pH 4.5 with 1N hydrogen chloride and extracted with chloroform to eliminate the aglycones. The aqueous solution, adjusted to pH 8.5, was repeatedly extracted with chloroform.

The combined chloroform extracts, after being dried over anhydrous sodium sulphate, were concentrated to 10 ml by evaporation. Addition of a stoichiometric amount of anhydrous methanolic hydrogen chloride and excess diethyl ether to the concentrated chloroform solution afforded the 3',4'-epi-6'-hydroxydaunomycin hydrochloride (V) (0.36 g; 83%): m.p. 183°–185° C; $[\alpha]_D = +215°$ ($c = 0.02$ in methanol). Thin layer chromatography on Merck Kieselgel HF buffered at pH 7 with M/15 phosphate, using a chloroform:methanol:water solvent system (13:6:1 by vol.) revealed a spot at Rf:0.43.

EXAMPLE 4

3',4'-epi-6'-hydroxy-adriamycin (VI)

The final product of Example 3 (0.3 g), dissolved in a mixture of 4.2 ml of anhydrous methanol and 12 ml of dioxane was mixed with 0.3 g of ethyl orthoformate and 1.1 ml of a solution of 0.93 g of bromine in 10 ml of chloroform. After one hour at room temperature, the reaction mixture was poured into a mixture of 60 ml of diethyl ether and 30 ml of petroleum ether (40°–70° C. bp). A red precipitate formed which was filtered and washed several times with diethyl ether to completely remove the acidity. The precipitate was then dissolved in a mixture of 6 ml of acetone and 6 ml of 0.25 N aqueous hydrogen bromide. After 15 hours at room temperature, the mixture was mixed with 6 ml of water and extracted repeatedly with chloroform to remove the aglycones. The aqueous phase was extracted with n-butanol until the extracts were no longer colored. Evaporation of the organic phase under vacuum to a small volume, i.e., about 5 ml, afforded 0.26 g of the 14-bromo derivative as a red crystalline product. The 14-bromo derivative (0.26 g) was dissolved in 6 ml of 0.25N aqueous hydrogen bromide and mixed with 0.45 g of sodium formate in 4.5 ml of water.

The reaction mixture was stirred at room temperature for 100 hours, and then evaporated to dryness under vacuum. The residue, dissolved in 120 ml of a chloroform:methanol mixture (2:1 v/v), was washed twice with 50 ml portions of 2.5% aqueous solution of sodium bicarbonate. The aqueous phase was extracted with chloroform until the extracts were no longer colored. The organic phase was combined with the chloroform extracts, dried over anhydrous sodium carbonate, and evaporated to a small volume (about 30 ml) under vacuum.

The red solution, adjusted to pH 3.5 with anhydrous methanolic hydrogen chloride, was mixed with excess diethyl ether to give 0.12 g of 3',4'-epi-6'-hydroxyadriamycin (VI) as the hydrochloride:m.p. 158°-160° C. dec.; $[\alpha]_D = +178°$ ($c = 0.01$ methanol). Thin layer chromatography on Merck Kieselgel buffered at pH 7 with M/15 phosphate, using a chloroform:,ethanol:water solent system(13:6:1 by vol.) revealed a spot at Rf:0.32. This step follows the procedure of British Patent Specification No. 1,217,133, owned by the unrecorded assignee hereof.

EXAMPLE 5

3',4'-epi-daunomycin (X)

0.29 g of daunomycinone in 30 ml of anhydrous methylene dichloride was mixed with 0.15 g of the pyranosyl chloride (VIII) and treated with 0.1 g of $AgSO_3CF_3$ with vigorous stirring overnight at room temperature. The product was worked up as in Example 3, and 0.185 g (65%) of the protected product (VII) was obtained; m.p. 245° C. Thin layer chromatography on Merck Kieselgel 60F$_{254}$ using a benzene:ethyl acetate solvent system (2:1 v/v) revealed a spot at Rf:0.3. Basic treatment in order to remove the protective groups as described in Example 3 gave the desired product (X) in quantitative yield; m.p. 180°-181° C; $[\alpha]_D^{20} = +243.5°$ ($c = 0.05$ methanol). Thin layer chromatography on Merck Kieselgel plates buffered at pH 7 with M/15 phosphate, using a chloroform:methanol:water solvent system (13:6:1 by vol.) revealed a spot at Rf:0.55. Daunomycin under the same conditions has an Rf of 0.43.

EXAMPLE 6

3',4'-epi-adriamycin (XI)

The product X (0.5 g) was transformed, as in Example 4, to its adriamycin analog (XI) (0.28 g) m.p. 168°-170° C; $[\alpha]_D^{20} = +284°$. ($c = 0.044$ methanol); Rf=0.3 using $CHCl_3:CH_3OH:H_2O$: 14:6:1 (vol.).

EXAMPLE 7

4-demethoxy-4'-epi-daunomycin (XIII)

One gram of 4-demethoxydaunomycinone* (described and claimed in our Patent Appln. Ser. No. 649,825, owned by the unrecorded assignee hereof) dissolved in 100 ml of anhydrous methylene chloride containing 1.2 g of 1-chloro-N,O-trifluoroacetyl-4-epi-daunosamine (described and claimed in Belgian Pat. Ser. No. 826,848, which is also owned by the unrecorded assignee hereof) was treated in the presence of 10 g of molecular sieve (4 Å Merck) with 0.86 g of $AgSO_3CF_3$ dissolved in 40 ml of diethyl ether. After 20 minutes at room temperature the reaction mixture was neutralized with a saturated aqueous solution of $NaHCO_3$ and the organic phase was separated and evaporated under vacuum. The resulting N,O protected glycoside (XII) was treated with 200 ml of methanol for 15 minutes at room temperature and the crude product (1.3 g) obtained by evaporating the solvent was chromatographed on a column of silicic acid using the mixture chloroform:benzene:methanol (100:30:4 by vol.) as the eluting agent. There was obtained 0.55 g of pure N-trifluoroacetyl-4-demethoxy-4'-epi-daunomycin. PMR ($CDCl_3$-DMSO-$d_6$ 1:1 v/v): 1.38 (d, $CH_3$-C-5'), 5.23 (broad s, $W_H$ 7.5Hz C-7 H), 5.5 (dd, J'~2.5 Hz, J"~1Hz, C-1'H), 7.7-8.0 and 8.15-8.50 (two symmetrical m, aromatic H), 13.18 and 13.45 (two s, C-6 OH and C-11 OH). Thin layer chromatography on Merck Kieselgel F$_{254}$ using the solvent system chloroform:benzene:methanol (100:30:4 v/v) revealed a spot at Rf:0.17.
* Formula I wherein R is hydrogen.

The N-trifluoroacetyl derivative was dissolved in 5 ml of acetone and treated at 0° C. with 50 ml of 0.1N NaOH. After 20 minutes the solution was adjusted to pH 8.2 and extracted repeatedly with chloroform. The combined chloroform extracts, after being dried and concentrated to a small volume (about 15 ml) were acidified to pH 3.5 with anhydrous methanolic hydrogen chloride. Upon addition of an excess of diethyl ether there was obtained 0.35 g of 4-demethoxy-4'-epi-daunomycin (XIII), as the hydrochloride: TLC on Merck Kieselgel F$_{254}$ using the solvent system chloroform:methanol:water (120:20:2) revealed a spot at Rf:0.25.

EXAMPLE 8

4-demethoxy-4'-epi-adriamycin (XIV)

0.35 g of 4-demethoxy-4'-epi-daunomycin hydrochloride (XIII) dissolved in a mixture of 5 ml of anhydrous methanol, 14 ml of dioxane and 0.35 ml of ethyl orthoformate was treated with 1.4 ml of a solution of 0.93 g of bromine in 10 ml of chloroform. After 30 minutes at room temperature the reaction mixture was poured into a mixture of 70 ml of ethyl ether and 35 ml of petroleum ether. The resulting red precipitate, after being filtered and washed with ethyl ether several times to completely remove the acidity was dissolved in a mixture of 7 ml of acetone and 6 ml of 0.25 N aqueous hydrogen bromide. After 15 hours at room temperature, 6 ml of water were added to the mixture and the solution was extracted several times with chloroform to remove the aglycones. Then, the aqueous phase was extracted with n-butanol until the extracts became colorless. Evaporation of the combined organic solvent extracts (n-butanol) under vacuum to a small volume (about 6 ml) yielded 0.26 g of the 14 -bromo derivative. This latter compound was dissolved in 6.7 ml of 0.25 N aqueous hydrogen bromide and treated with 0.5 g of sodium formate in 5 ml of water. The reaction mixture was kept at room temperature with stirring for 48 hours, and was then evaporated to dryness under vacuum. The resulting residue, dissolved in 120 ml of a chloroform:methanol (2:1 v/v) mixture was washed twice with 50 ml portions of a 2.5% aqueous solution of NaHCO$_3$. The aqueous phase was repeatedly extracted with chloroform until the extracts were colorless. The combined chloroform extracts were dried with Na$_2$SO$_4$ and evaporated to a small volume (about 30 ml) under vacuum. The resulting red solution, adjusted to pH 3.5 with anhydrous methanolic hydrogen chloride, was added with excess ethyl ether to give 0.17 g of 4-demethoxy-4'-epi-adriamycin (XIV), as the hydrochloride. The hydrochloride was purified by chromatography on a column of cellulose powder using chloroform:methanol:water (140:20:2 v/v/) as the eluting agent. The pure product melts with decomposition at 178° C; TLC on Merck Kieselgel F$_{254}$ buffered at pH 7 with M/15 phosphate, using chloroform:methanol:water (130:60:10 v/v) as the solvent revealed a spot at Rf:0.54.

EXAMPLE 9

4'-epi-daunomycin

Daunomycinone (6 g; 15 mmols) was dissolved in 700 ml of anhydrous methylene dichloride and mixed with 2.3 g; 9.4 mmol of 1-chloro-N,O-trifluoroacetyl-4-epi-daunosamine (described and claimed in Belgian Patent Ser. No. 826,848, owned by the unrecorded assignee hereof), and 20 g of molecular sieve (4 A Merck).

A solution of 2.6 g; 10 mmols of AgSO$_3$CF$_3$ in 50 ml of diethyl ether was added to the above mixture, with stirring, over 30 minutes at room temperature. After two hours, the reaction mixture, after being neutralized with a saturated aqueous solution of sodium bicarbonate was filtered. The organic phase was separated, evaporated to 100 ml and then treated with 300 ml of methanol for 12 hours at room temperature. The residue, obtained by evaporation of the solvents under vacuum, was chromatographed on a column of silicic acid using a chloroform:benzene:methanol mixture (100:20:4 v/v) as the eluting agent. In addition to 2.4 g of unreacted daunomycinone, 1.0 g of a mixture of daunomycinone and N-trifluoroacetyl-4'-epi-daunomycin, and 4.4 g of pure N-trifluoroacetyl-4'-epi-daunomycin were obtained. This last compound (4.4 g) was dissolved in 260 of 0.1 N sodium hydroxide. After 20 minutes at room temperature, the solution was adjusted to pH 8.2 and repeatedly extracted with chloroform. The combined chloroform extracts were concentrated to a small volume (about 50 ml), acidified to pH 3.5 with anhydrous methanolic hydrogen chloride and mixed with an excess of diethyl ether. The precipitated 4'-epi-daunomycin hydrochloride was filtered off, washed with diethyl ether, and dried under vacuum. The product (3.0 g) was identical in all respects with that described and claimed in copending application Ser. No. 560,105, filed Mar. 19, 1975, owned by the unrecorded assignee hereof.

EXAMPLE 10

Daunomycin 2.4 g (6 mmol) of daunomycinone were dissolved in 300 ml of anhydrous methylene dichloride and mixed with 1.1 g (3.08 mmol) of 1-chloro-N,O-trifluoroacetyl-daunosamine (described and claimed in Belgian Patent Ser. No. 826,848, owned by the unrecorded assignee hereof), and 10 g of molecular sieve (4 Å Merck). The solution was mixed with 0.77 g of AgSO$_3$CF$_3$ (3 mmols) in 20 ml of anhydrous diethyl ether with vigorous stirring for 30 minutes. After two hours at room temperature, the reaction mixture was neutralized with a saturated aqueous solution of sodium bicarbonate and the organic phase was separated and evaporated under vacuum. The residue was dissolved in 200 ml of methanol and kept at room temperature for five hours.

The residue remaining after removal of the solvent was chromatographed on a column of silicic acid using a chloroform:methanol mixture (100:3 v/v) as the eluting agent. In addition to 1.1 g of unreacted daunomycinone, 1.2 g of N-trifluoroacetyldaunomycin were obtained. This compound (1.0 g) was dissolved in 100 ml of 0.1N aqueous sodium hydroxide and after 30 minutes at room temperature, the solution was adjusted to pH 8.6 and repeatedly extracted with chloroform. The combined chloroform extracts, after being dried over anhydrous sodium sulphate, were concentrated to a small volume and acidified to pH 4.5 with 0.1N methanolic hydrogen chloride to allow crystallization of daunomycin hydrochloride, which proved to be identical in all respects with the product obtained be fermentation. The yield was practically quantitative.

Biological activity

The antitumor activity of the novel compounds of the invention, i.e., 3'-4'-epi-daunomycin, 3'-4'-epi-6'-hydroxydaunomycin, 3'-4'-epi-6'-hydroxyadriamycin and 4-demethoxy-4'-epi-adriamycin was evaluated on several transplanted tumors in mice, and in in vitro tests. The results of these tests are given in the following tables.

(A) 3'-4'-epi-daunomycin

Test in vitro of the cloning efficiency of Hela cells

After treatment for 2, 8 and 24 hours, Hela cells were seeded (200 cells per plate) and the number of colonies determined 8 days later. The inhibiting dose (ID$_{50}$) represents the does which produces a 50% inhibition of colonies.

TABLE 1

(Action on Hela cells)

| COMPOUND | ID$_{50}$(μg/ml) | | |
|---|---|---|---|
| | 2 hours | 8 hours | 24 hours |
| Daunomycin | 17 | 8.5 | 6.8 |
| 3'-4'-epi-daunomycin | 270 | 220 | 190 |

Test in vitro on the formation of foci by Moloney Sarcoma Virus (MSV)

The test compound was evaluated on mouse embryo fibroblast (MEF) cultures infected with MSV and on similar uninfected cultures. After a treatment of three days the inhibiting doses (ID$_{50}$) were evaluated on cell proliferation in uninfected cultures (cytotoxic action) and on MSV foci formation in infected cultures (antiviral action).

TABLE 2

| COMPOUND | Antiviral action ID$_{50}$(ng/ml) | Cytotoxic action ID$_{50}$(ng/ml) |
|---|---|---|
| Daunomycin | 3 | 16 |
| 3'-4'-epi-daunomycin | 45 | 90 |

The compound 3'-4'-epi-daunomycin shows less cytotoxic acitivity in vitro, when compared with daunomycin. In tumor bearing animals, however, this compound shows a distinct anti-tumor activity as shown in Table 3.

Ascites lymphocitic P 388 Leukemia

Male $CDF_1$ mice were intraperitoneally inoculated with $6\times 10^6$ leukemia cells/mouse and then treated intraperitoneally from the first to the ninth day after inoculation with different doses of the compound 3'-4'-epi-daunomycin. Evaluation was made on the twentieth day.

TABLE 3

| Dose (mg/kg) | Toxicity (survivors at fifth day) | Cures | Weight Difference | Tumor evaluation median survival time (days) (*) | T/C % |
| --- | --- | --- | --- | --- | --- |
| 25 | 6/6 | 1 | −0.8 | 28 | 231 |
| 12.5 | 6/6 | — | −0.1 | 21 | 173 |
| 6.25 | 6/6 | — | +0.7 | 18.8 | 155 |
| 3.13 | 6/6 | — | +0.3 | 17.3 | 142 |
| 1.56 | 6/6 | — | +1.0 | 15.7 | 129 |

(*) Control = 12.1 days (B) 3'-4'-epi-6'-hydroxydaunomycin

This compound exhibits significant in vivo activity as shown in Table 4 indicating the effect of the compound on L 1210 leukemia bearing mice.

Inbread BDF mice were intraperitoneally inoculated with $1\times 10^5$ leukemia cells/mouse and then treated with 3'-4'-epi-6'-hydroxydaunomycin: Single treatment i.p. on the first day.

TABLE 4
(Action on L1210 Leukemia)

| COMPOUND | Dose (ng/Kg) | T/C % |
| --- | --- | --- |
| 3'-4'-epi-6'-hydroxydaunomycin | 7.5 | 150 |
|  | 11.5 | 150 |
|  | 17.25 | 150 |

(C) 3'-4'-epi-6'-hydroxyadriamycin

This compound has been found to be active in experimental tumors. In Table 5 the activity of 3'-4'-epi-6'-hydroxyadriamycin on Ascites Sarcoma 180 in mice is reported. The test was carried out on groups of 10 mice (Swiss CD1). The compound under examination was administered intraperitoneally in varying doses to the test animals one day after intraperitoneal inoculation with $1\times 10^6$ tumor cells/mouse.

The average survival time is given as percentage of the survival time of untreated animals, which is arbitrarily designated as 100%. The number of long term survivors (LTS) is also reported.

TABLE 5
(Action on Ascites Sarcoma 180)

| COMPOUND | Dose (ng/Kg) | T/C % | LTS |
| --- | --- | --- | --- |
| 3'-4'-epi-6'-hydroxyadriamycin | 3 | 123 | 1/10 |
|  | 4.5 | 226 | 2/10 |
|  | 6.7 | 138 |  |
|  | 10.5 | 138 |  |
| adriamycin | 4.5 | 250 | 1/10 |

(D) 4-Demethoxy-4'-epi-adriamycin

The above compound was tested in comparison with adriamycin in several in vitro systems and experimental mouse tumors. The in vitro results are reported in Table 6. The test compound was found to be definitely more active than adriamycin.

The results obtained on experimental mouse tumors are reported in Tables 7, 8 and 9.

In all the systems tested, 4-demethoxy-4'-epi-adriamycin displayed a remarkable antitumor activity at doses 10 times lower than adriamycin.

On L 1210 and P 388 leukemias, the antitumor activity at the optimal (non-toxic) dose was comparable to that of adriamycin. On solid sarcoma 180, the inhibition of tumor growth on the eleventh day was slightly lower than that of adriamycin, at equitoxic doses. On Gross leukemia (which is a systemic tumor transplanted i.v.), the increase in the life span of mice treated with the two compounds at equitoxic doses was similar.

It can therefore be concluded that 4-demethoxy-4'-epi-adriamycin displayed a higher antitumor activity in mice, similar to adriamycin, at doses lower by a factor of 10.

TABLE 6
In vitro effect of 4-demethoxy-4'-epi-adriamycin, in comparison with adriamycin $ID_{50}$(ng/ml)

| COMPOUND | HeLa[a] 2[a] | 8 | 24 | MSV[b] 72 | MEF[c] 72 |
| --- | --- | --- | --- | --- | --- |
| Adriamycin | 125 | 28 | 12.5 | 0.01 | 0.026 |
| 4-demethoxy-4'-epi-adriamycin | 0.35 | 0.1 | 0.03 | <0.003 | <0.003 |

[a] cloning efficiency of Hela cells
[b] inhibition of MSV foci formation
[c] inhibition of mouse embryo fibroblasts proliferation

TABLE 7
Activity of 4-demethoxy-4'-epi-adriamycin on ascitic leukemias. Treatment i.p. on day 1.

| Leukemia | Compound | Dose (mg/Kg) | T/C[a] % | LTS[b] | Toxic deaths |
| --- | --- | --- | --- | --- | --- |
| L 1210 | Adriamycin | 2.5 | 155 | 4/11 | 0/11 |
|  |  | 5 | 166 | 1/11 | 1/11 |
|  |  | 10 | 155 | 3/11 | 7/11 |
|  | 4-demethoxy-4'-epi-adriamycin | 0.25 | 155 | 0/11 | 0/11 |
|  |  | 0.5 | 166 | 2/11 | 0/11 |
|  |  | 1 | 133 | 0/11 | 11/11 |
| P 388 | Adriamycin | 2.5 | 150 | 0/10 | 0/10 |
|  |  | 5 | 162 | 0/10 | 0/10 |
|  |  | 10 | 200 | 1/10 | 0/10 |
|  | 4-demethoxy-4'-epi-adriamycin | 0.25 | 143 | 0/10 | 0/10 |
|  |  | 0.5 | 162 | 1/10 | 1/10 |
|  |  | 1 | 162 | 0/10 | 8/10 |

[a] Median survival time, % over untreated controls
[b] Long term survivors at 60 days

TABLE 8
Activity of 4-demethoxy-4'-epi-adriamycin on solid sarcoma 180. Treatment i.v. on days 1 to 5. Average data of 2 experiments.

| COMPOUND | Dose (mg/Kg) | T/C[a] % | Toxic deaths |
| --- | --- | --- | --- |
| Adriamycin | 2 | 22.2 | 3/19 |
|  | 2.5 | 13.5 | 11/18 |
| 4-demethoxy-4'-epi-adriamycin | 0.06 | 87.3 | 0/10 |
|  | 0.12 | 85.1 | 2/16 |
|  | 0.25 | 41.9 | 4/19 |
|  | 0.5 | — | 9/9 |

[a] Tumor weight on day 11, % over untreated controls.

TABLE 9
Activity of 4-demethoxy-4'-epi-adriamycin on Gross leukemia. Treatment i.v. on days 1 to 3. Average data of 2 experiments[a].

| COMPOUND | Dose (mg/Kg) | T/C % | LTS | Toxic deaths |
| --- | --- | --- | --- | --- |
| Adriamycin | 3.5 | 164 | 0/20 | 0/20 |

TABLE 9-continued

Activity of 4-demethoxy-4'-epi-adriamycin on Gross leukemia. Treatment i.v. on days 1 to 3.
Average data of 2 experiments[a].

| COMPOUND | Dose (mg/Kg) | T/C % | LTS | Toxic deaths |
|---|---|---|---|---|
|  | 4.5 | 182 | 0/20 | 0/20 |
|  | 5.5 | 200 | 1/10 | 1/10 |
|  | 6 | 214 | 0/10 | 3/10 |
| 4-demethoxy-4'-epi-adriamycin |  |  |  |  |
|  | 0.35 | 153 | 2/20 | 0/10 |
|  | 0.45 | 196 | 0/20 | 0/20 |
|  | 0.55 | 186 | 0/10 | 0/10 |
|  | 0.6 | 214 | 0/10 | 1/10 |
|  | 0.65 | 207 | 0/10 | 0/10 |

[a]See legends to Table 7.

Variations can, of course, be made without departing from the spirit and scope of the invention.

Having thus described the invention, what is desired to be secured by Letters Patent and hereby claimed is:

1. A glycosidic compound selected from the group consisting of 3'-4'-epi-6'-hydroxy-daunomycin; 3'-4'-epi-6'-hydroxy-adriamycin; 3'-4'-epi-daunomycin; 3'-4'-epi-adriamycin; 4-demethoxy-4'-epi-daunomycin and 4-demethoxy-4'-epi-adriamycin.

2. A compound according to claim 1, which is 3'-4'-epi-6'-hydroxy-daunomycin ($\alpha$ anomer).

3. A compound according to claim 1, which is 3'-4'-epi-6'-hydroxy-adriamycin ($\alpha$ anomer).

4. A compound according to claim 1, which is 3'-4'-epi-daunomycin ($\alpha$ anomer).

5. A compound according to claim 1, which is 3'-4'-epi-adriamycin ($\alpha$ anomer).

6. A compound according to claim 1, which is 4-demethoxy-4'-epi-daunomycin ($\alpha$ anomer).

7. A compound according to claim 1, which is 4'-demethoxy-4'-epi-adriamycin ($\alpha$ anomer).

8. A method of inhibiting the growth of a tumor selected from the group consisting of Moloney Sarcoma Virus, Ascites lymphocitic P. 388 leukemia, L1210 leukemia, Ascites Sarcoma 180 and Solid Sarcoma 180 which comprises intraperitoneally administering to a host afflicted with said tumor an amount of a compound selected from the group consisting of 3'-4'-epi-6'-hydroxy-daunomycin; 3'-4'-epi-6'-hydroxy-adriamycin; 3'-4'-epi-duanomycin; 3'-4'-epi-adriamycin; 4-demethoxy-4'-epi-daunomycin and 4-demethoxy-4'-epi-adriamycin sufficient to inhibit the growth of said tumor.

* * * * *

UNITED STATES PATENT OFFICE
CERTIFICATE OF CORRECTION

Patent No. 4,112,076          Dated September 5, 1978

Inventor(s) Federico Arcamone et al

It is certified that error appears in the above-identified patent and that said Letters Patent are hereby corrected as shown below:

Column 3, line 26: "compounds" should read -- compound --.

Column 5, line 20: "(where" should read -- (when --; line 23: "daunosamine (this" should read -- -epi-daunosamine (this --.

Column 8, line 21: "-α-L-erthro-" should read -- -α-L-erythro- --.

Column 9, line 17: "braod" should read -- broad --; line 29: "6.45α" should read -- 6.45δ --; line 48: "20%20" should read -- 20% --.

Column 10, line 2: "chromatography of" should read -- chromatography on --; line 33: "obtain" should read -- obtained --.

Column 11, line 29: "chloroform:,ethanol:" should read -- chloroform:ethanol: --.

Column 13, line 41: "260" should read -- 260 ml --.

Column 14, line 18: "be fermentation" should read -- by fermentation --; line 36: "does" should read -- dose --.

UNITED STATES PATENT OFFICE
CERTIFICATE OF CORRECTION

Patent No. 4,112,076  Dated September 5, 1978

Inventor(s) Federico Arcamone et al

It is certified that error appears in the above-identified patent and that said Letters Patent are hereby corrected as shown below:

Column 15, line 24: "Inbread" should read -- Inbred --.

Signed and Sealed this

Nineteenth Day of June 1979

[SEAL]

Attest:

RUTH C. MASON
*Attesting Officer*

DONALD W. BANNER
*Commissioner of Patents and Trademarks*